United States Patent [19]  [11] 3,959,399
Bridwell et al.  [45] May 25, 1976

[54] MONO-ALKYLATION OF NAPHTHALENE
[75] Inventors: B. W. Bridwell; Carl E. Johnson, both of Brookhaven, Miss.
[73] Assignee: Nalco Chemical Company, Oak Brook, Ill.
[22] Filed: Feb. 19, 1975
[21] Appl. No.: 551,431

[52] U.S. Cl. .................. 260/671 C; 260/671 B; 260/671 P; 260/671 R
[51] Int. Cl.² ........................................ C07C 3/54
[58] Field of Search .......... 260/671 R, 671 C, 67 B, 260/67 P

[56] References Cited
UNITED STATES PATENTS
2,006,695   7/1935   Ipatieff ................................. 260/671
2,014,766   9/1935   Isham .................................. 260/671
2,777,007   1/1957   Skinner et al ....................... 260/671
3,293,315   12/1966  Nixon .................................. 260/671

Primary Examiner—Delbert E. Gantz
Assistant Examiner—C. E. Spresser
Attorney, Agent, or Firm—John G. Premo; John S. Roberts

[57] ABSTRACT

In the alkylation of naphthalene using an alkene reactant to produce monoalkyl naphthalene, the inhibition of polyalkyl and specially dialkyl naphthalenes by the use of a mixed protonic acid catalyst consisting of methane sulfonic acid and an active $P_2O_5$ containing acid, utilized in about a 2:1 to 1:2 ratio with an optimum ratio of about 1:1. The reaction is carried out preferably under anhydrous conditions with respect to the mixed catalyst, and the products show present utility as emulsion breakers in petroleum chemistry as well as other surface active agents.

4 Claims, No Drawings

MONO-ALKYLATION OF NAPHTHALENE

The present invention relates generally to the alkylation of polycyclic aromatic compounds and especially to naphthalene reacted with α-olefins with a carbon length C$_4$–C$_{16}$. In the past where simple catalysts were utilized, the reaction was often termed a Friedel-Crafts reaction, but in the present setting where a mixed catalyst is used, the reaction is referred to simply as the alkylation of an aromatic compound in the liquid phase. As process fingerprint data, the present reaction is conducted generally at atmospheric pressure and slightly elevated temperatures of from 70°–170°C, depending on molar concentration of alkene and catalyst concentration. With 30% by weight catalyst an initiating temperature of 70°C was noted and with 15% by weight catalyst an initiating temperature of 115°C was noted. The reaction is also exothermic in nature and a 50°–60°C "heat kick" is engendered during the alkylation. The central facet of the present process depends upon a novel mixed catalyst which utilizes an alkane sulfonic acid which, in an optimum ratio, is combined with an equal amount of phosphoric acid such as orthophosphoric acid, pyrophosphoric acid, or preferably polyphosphoric acid, wherein the P$_2$O$_5$ content of the phosphoric acid is enhanced. The general subject matter is covered adequately in George A. Olah, *Friedel-Crafts and Related Reactions*, Vol. 2, Part 1, 1964, Interscience-Wiley, pages 1–31, 69–71, and Tables 25–29 (pages 180–186), relating to the reactions of naphthalenes with olefins.

PRIOR ART

U.S. Pat. No. 2,541,882 Moore (Shell Development) — Aluminum chloride used for naphthalation by alkylene.

U.S. Pat. No. 2,754,341 Kirkland (American Oil) — Phosphoric acid saturated with BF$_3$ (UOP poly catalyst) used for alkylation of aromatic hydrocarbons.

British Pat. No. 616,260 — Iron phosphate and a phosphoric acid catalyst utilized at high temperatures and pressures for mono-directional ethylation of naphthalene as in Example 9. This system is a solid and contains iron.

George A. Olah, *Friedel-Crafts and Related Reactions*, Vol. 2, Part 1, 1964, Interscience-Wiley, pages 1–31; 69–71; 180–186 — Reactions of naphthalenes with olefins.

Kirk-Othmer, *Encyclopedia of Chemical Technology*, II, 13, Interscience-Wiley, 1967, page 674 — Alkylation of naphthalene with sulfuric acid.

Irvin Rothberg and H. Martin Friedman, "The Synthesis of Some t-Alkylnaphthalenes," *Synthetic Communications*, 4(5), 259–264 (1974) — Mono-alkylation of naphthalene with olefins using boron trifluoride-phosphoric acid as a catalyst and particularly producing t-alkylnaphthalenes.

STARTING MATERIALS

Naphthalene

Naphthalene is a well known bicyclic aromatic with the following structure:

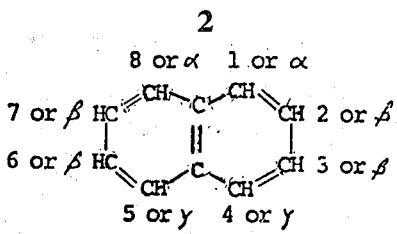

Under mild conditions as is present here, disubstitution production produces the 1,4-disubstituted product. The thrust of the present invention lies in the inhibition of di- and polysubstitution on naphthalene by utilization of a mixed protonic acid catalyst and further the function of the phosphoric acid fraction of the catalyst acts to inhibit poly-substitution on the aromatic nucleus. Although the rate of reaction is somewhat slower than a similar reaction proceeding to disubstitution, the present reaction is capable of proceeding to completion or exhaustion of naphthalene under the conditions set out. It is further noted that in Table I, post, a methane sulfonic acid (MSA) catalyst acting alone and without phosphoric acid is not positively directional either to mono- or disubstitution showing a product distribution of 64/28 mono/di in the presence of 1.25 moles of hexene and 29.5/70.3 mono/di product in the presence of 2.5 moles of hexene.

α-OLEFIN

The α-olefin is selected from a C$_4$–C$_{16}$ olefin where the double bond is terminal or at the 1-position. The olefin may be of the straight chain or branch chain type. Selected members include octene-1, nonene-1, decene-1, dodecene-1, tetradecene-1, hexadecene-1, and branch chain olefins such as diisobutylene, diisohexylene, etc. In terms of commercial availability and particular adaption to certain required surfactant qualities, the straight chain unsaturated aliphatics are preferred to the branch chain varieties.

Alkane Sulfonic Acid Fraction of the Catalyst

In the mixed catalyst an alkane sulfonic acid fraction is the moving force in the alkylation. Such a catalyst is, for example, selected from butane sulfonic acid, ethane sulfonic acid, and preferably methane sulfonic acid (MSA). It has been found (Olah, page 25 ante) that the utilization of the sulfonic acid catalyst is preferable to using a sulfuric acid, since the latter is prone to enter into competing reactions which produce sulfonated products on the aromatic ring. Kirk-Othmer, *Encyclopedia of Chemical Technology*, II, 13, Interscience-Wiley, 1967, page 674, also comments relative to the alkylation of naphthalene with sulfuric acid, "if acid of sufficient strength is used, alkylation and sulfonation on the ring take place simultaneously and alkylene naphthalene sulfonic acids are produced."

It has been further found that the methane sulfonic acid (MSA) is inactivated in the presence of water which is obviated by removing water from commercial methane sulfonic acid (MSA) and the avoidance of sulfuric acid as a catalyst, since this latter produces water in the sulfonation reaction.

Phosphoric Acid Fraction of the Catalyst

The inhibition of polycyclic substitution on the aromatic ring of naphthalene is achieved by utilization of a phosphoric acid which may be orthophosphoric acid, or a condensed phosphoric acid such as pyrophosphoric or polyphosphoric acid. Condensed phosphoric acids are defined in John R. VanWazer, *Phosphorus*

*and Its Compounds*, Vol. I, Interscience-Wiley, 1966, page 770. Such condensed phosphoric acids, which are preferable for the present invention, are defined by VanWazer as a ratio $H_2O/P_2O_5$ giving mole ratios of 1.4/2.3 and listing specifically pyrophosphoric acid $2H_2O \cdot P_2O_5$ and crystalline tetraphosphoric acid $3H_2O \cdot 2P_2O_5$. The presence of the phosphoric acid fraction in the catalyst as it approaches equivalence to that utilized for MSA gives strong inhibitory action to the combination.

In Table I below are shown the relative inhibition phosphoric acid when utilized 10/90 with MSA and the greater effectiveness where the same catalyst is used in a ratio of 60/40 with MSA.

TABLE I

Alkylation of Napthalene with Mixed Catalysts

| Catalyst | Moles Hexene-1 Addition | Product Distribution-Area % | | |
|---|---|---|---|---|
| | | Naph. | Mono-* | Di-* |
| 60/40 | 1.25 | 12.4 | 87.6 | tr. |
| PP/MS** | 2.50 | 0.5 | 99.5 | tr. |
| 10/90 | 1.25 | 10.7 | 84.7 | 4.6 |
| PP/MS | 2.50 | tr. | 46.7 | 53.3 |
| MS | 1.25 | 7.7 | 64.3 | 28.0 |
| | 2.50 | 0.2 | 29.5 | 70.3 |

*mono- and di- represent the mono- and di-hexyl derivatives of naphthalene.
**PP is notation for polyphosphoric acid and MS is notation for anhydrous methane sulfonic acid.

In the above, polyphosphoric acid is utilized with anhydrous methane sulfonic acid (MSA) in the reaction of 1 mole of naphthalene with hexene-1.

The Mixed Catalyst

The mono-directing mixed catalyst of the present invention as applied to the alkylation of naphthalene is utilized in weight percent ratios ranging from about 2:1 MSA/PP to 1:2 MSA/PP. The lower delimiting amount is governed by the amount of inhibition of bicyclic products and the upper amount is governed by the ability of the mixed catalyst to function as an alkylation catalyst. Also, a catalyst load of 15–30% based on weight percent of naphthalene has also been found operable in this process.

GENERALIZED PROCEDURE FOR PRODUCING ALKYL NAPHTHALENES

The generalized procedure for producing alkyl naphthalenes using as an example mono- and dihexyl naphthalenes is as follows.

1. One mole of naphthalene was charged to the reactor equipped with an agitator and facility for inert gas blanketing.
2. 0.2 mole anhydrous methane sulfonic acid (MSA) was added (15% w/w catalyst charge based on naphthalene).
3. 0.5 mole hexene-1 was added to the mixture and the reactor was blanketed with an inert gas purge (nitrogen or argon).
4. The mixture was heated with high agitation until the reaction initiated. This occurred at 100°–110°C and was marked by a 40°–50°C heat kick.
5. An additional 2 moles hexene-1 was added at a rate which maintained reaction temperature at 150°–170°C.
6. After hexene addition was completed, the mixture was agitated for an additional one-half hour.

A product was obtained which had a specific gravity of 0.88 and contained about 0.33 weight percent acid. The catalyst used above can be reused for the next batch with a makeup of about 5% per run. The product analysis was conducted via a gas chromatograph utilizing an 18 inch 20% Carbowax 20M on 60/80 mesh Chromosorb GAS DMCS programmed from 135°C (at injection) to 220°C at 32°C/minute. The GC was equipped with a thermal conductivity detector.

EXAMPLE I 128 g (1M) naphthalene, 20g anhydrous methane sulfonic acid, 21 g polyphosphoric acid (mol.wt. about 338) and 56 g (0.5M) octene-1 added to 1liter glass reactor, heated and stirred. 168 g (1.5M) additional octene-1 added over 2 ½ hour period at 60°–160°C. Gas chromatographic analysis showed about 2% residual naphthalene and 98% predominantly monooctyl-naphthalene and only trace amounts of polysubstituted naphthalene.

EXAMPLE II 128 g naphthalene, 27 g polyphosphoric acid, 20 g anhydrous methane sulfonic acid, 40 g hexene-1 added to flask, heated and stirred. 170 g additional hexene-1 was added over a 4 hour period at 120°–160°C. Naphthalene conversion was over 99% to a product that is greater than 95% monohexyl-naphthalene and barely detectable amounts of disubstituted naphthalene.

EXAMPLE III 128 g (1M) naphthalene, 20 g anhydrous methane sulfonic acid and 40 g (ca. 1/2 M) hexene-1 were added to 1liter flask, heated and stirred. Another 170 g (2M) hexene-1 was added over a 1 hour period at 105°–155°C. Gas chromatographic analysis showed a 99% conversion to a product containing 29% monohexylnaphthalene and 70% dihexylnaphthalene.

What is claimed is:

1. In a process of making mono- and polyalkyl naphthalenes by a reaction under anhydrous conditions in the liquid phase at moderate temperatures and at atmospheric pressure by reacting naphthalene with an α alkene having a carbon chain length of $C_4$–$C_{16}$ in the presence of a protonic acid catalyst, the improvement which consists of inhibiting the production of polyalkyl naphthalenes by utilizing a mixed protonic acid catalyst consisting of an alkane sulfonic acid and an active $P_2O_5$ containing acid catalyst utilized in a ratio of about 2:1 to 1:2 in weight percent of sulfonic acid:$P_2O_5$ containing acid catalyst.
2. The process of claim 1 wherein the mixed catalyst contains about a 1:1 ratio by weight percent of alkane sulfonic acid to an active $P_2O_5$ containing acid catalyst.
3. The process of claim 1 wherein the alkane sulfonic acid catalyst is methane sulfonic acid.
4. The process of claim 1 wherein the active $P_2O_5$ containing acid catalyst is polyphosphoric acid.

* * * * *